United States Patent [19]

Karlson

[11] Patent Number: 4,517,159
[45] Date of Patent: May 14, 1985

[54] STERILIZER

[76] Inventor: Eskil L. Karlson, 4634 State St., Erie, Pa. 16509

[21] Appl. No.: 510,552

[22] Filed: Jul. 5, 1983

[51] Int. Cl.³ .......................... A61L 2/00; A61L 2/02; A61L 2/20

[52] U.S. Cl. ...................................... 422/20; 422/28; 422/30; 422/31

[58] Field of Search .................. 422/20, 27, 28, 29, 422/30, 31, 35, 37, 127, 128

[56] References Cited

U.S. PATENT DOCUMENTS 3,549,528 12/1970 Armstrong ................... 422/28 X
3,719,017 3/1973 Shapiro et al. ............... 422/28 X
3,751,225 8/1973 Karlson ........................ 422/27 X

OTHER PUBLICATIONS

Boucher, R. M. G., "Ultrasonics", A Tool to Improve Biocidal Efficacy of Sterilants . . . Dental Practice; Canadian J. of Pharmaceutical Sciences; vol. 14, No. 1, 1979, pp. 1–12.

Primary Examiner—Barry S. Richman
Assistant Examiner—William R. Johnson
Attorney, Agent, or Firm—Ralph Hammar

[57] ABSTRACT

A method of sterilization for hospital and field use in which an article to be sterilized is submerged in water and ozone, which is supplied from a separate source, is bubbled through said water and over said article so as to provide an ozone concentration in excess of water saturation alone. Such a process can be used to kill even the most difficult bacteria and spores in shorter times than ethylene oxide sterilizers and further can be used for instruments which cannot stand steam temperatures or pressure changes.

13 Claims, 9 Drawing Figures

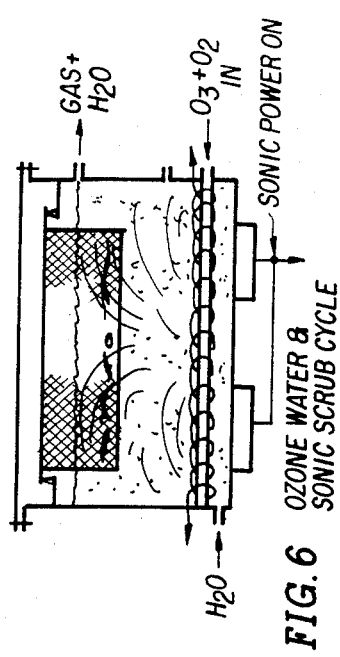
FIG. 3 LOADING CYCLE
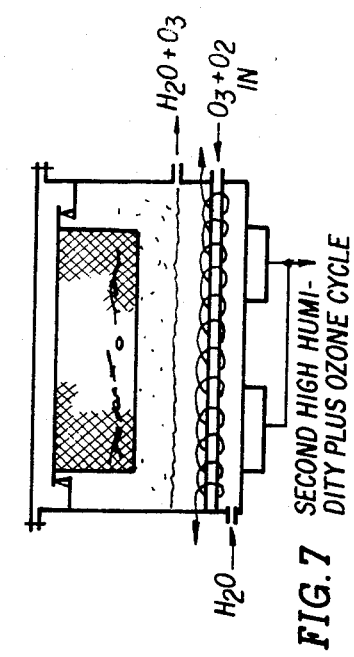
FIG. 4 OZONE HIGH HUMIDITY CYCLE
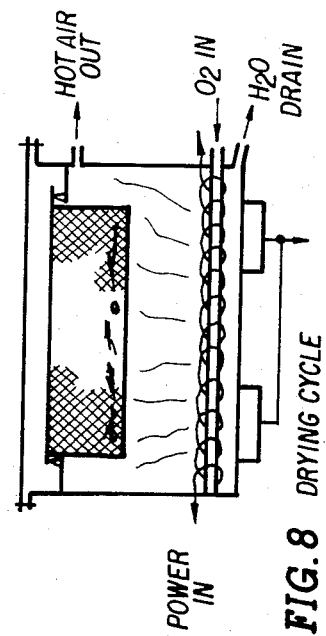
FIG. 5 OZONE WATER SCRUB CYCLE
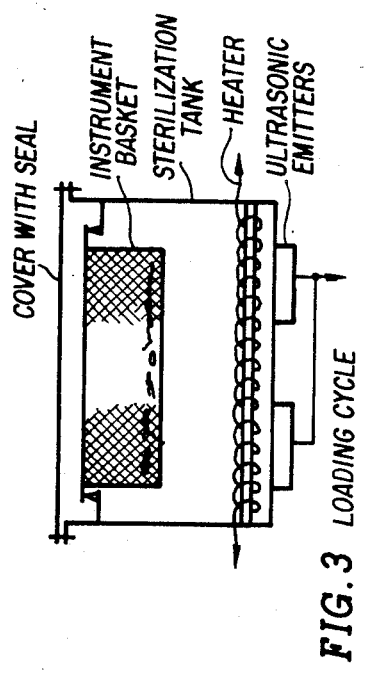
FIG. 6 OZONE WATER & SONIC SCRUB CYCLE
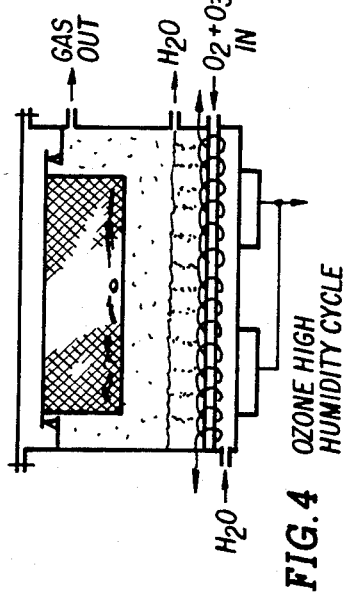
FIG. 7 SECOND HIGH HUMIDITY PLUS OZONE CYCLE
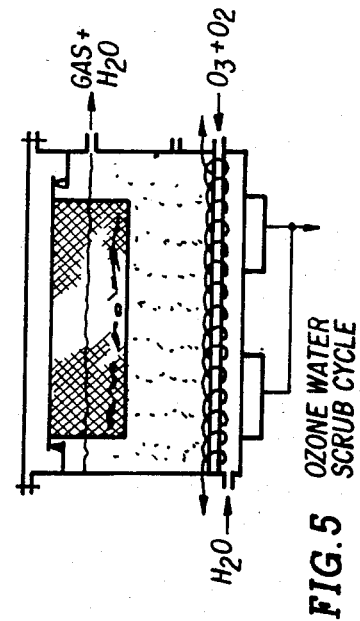
FIG. 8 DRYING CYCLE
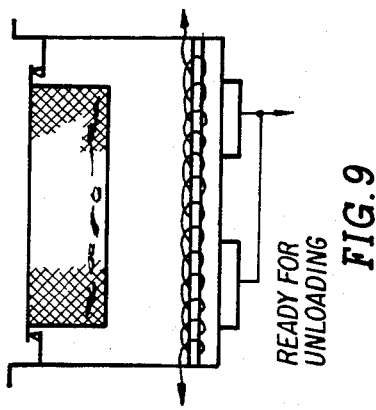
FIG. 9 READY FOR UNLOADING

STERILIZER

This invention is an improvement on U.S. Pat. No. 3,719,017. It is intended to simplify the operation and increase the effectiveness by the concurrent use of ultrasonic vibration to dislodge bacteria and expose underlying bacteria to the sterilizing agent.

Figure 1:
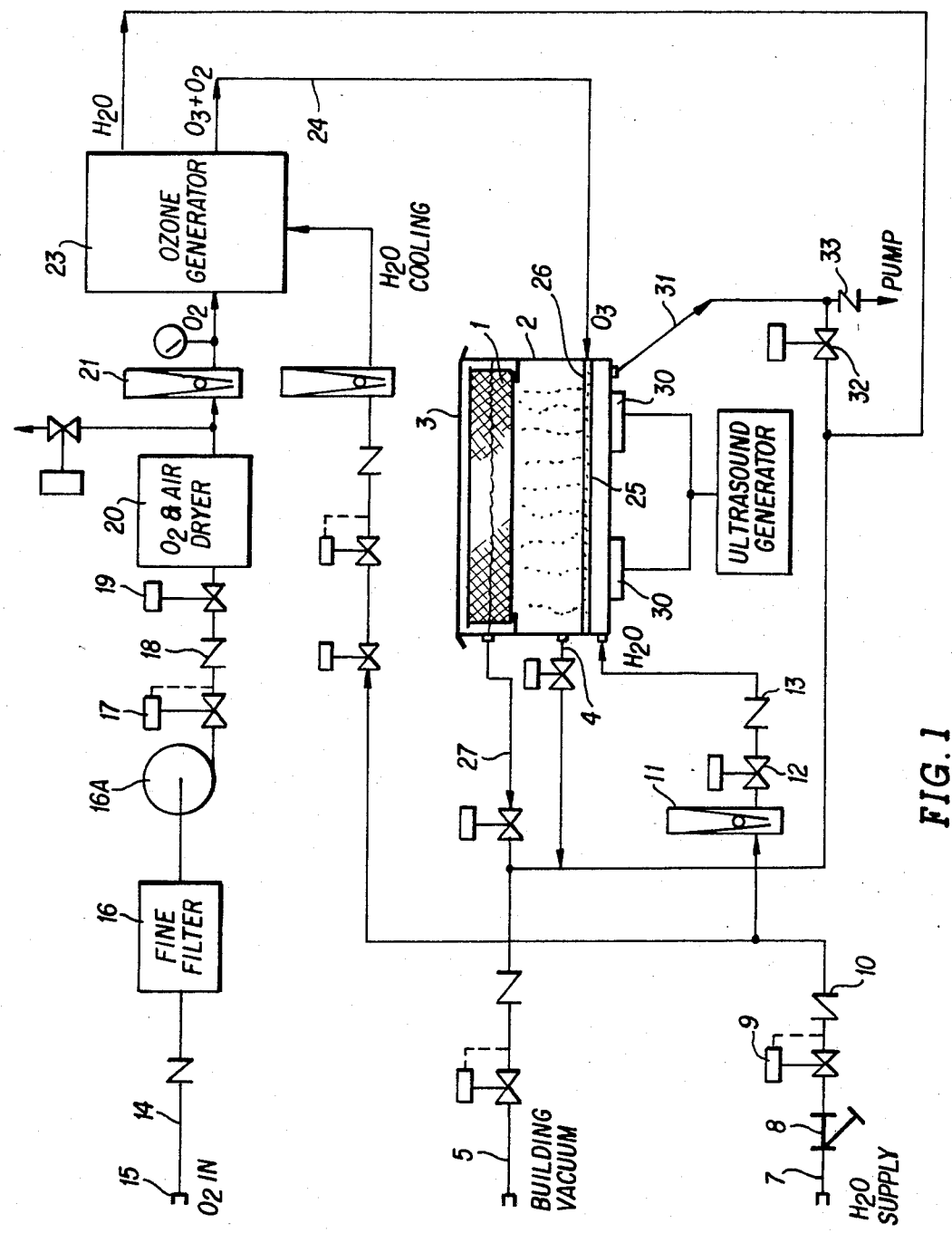
Figure 2:
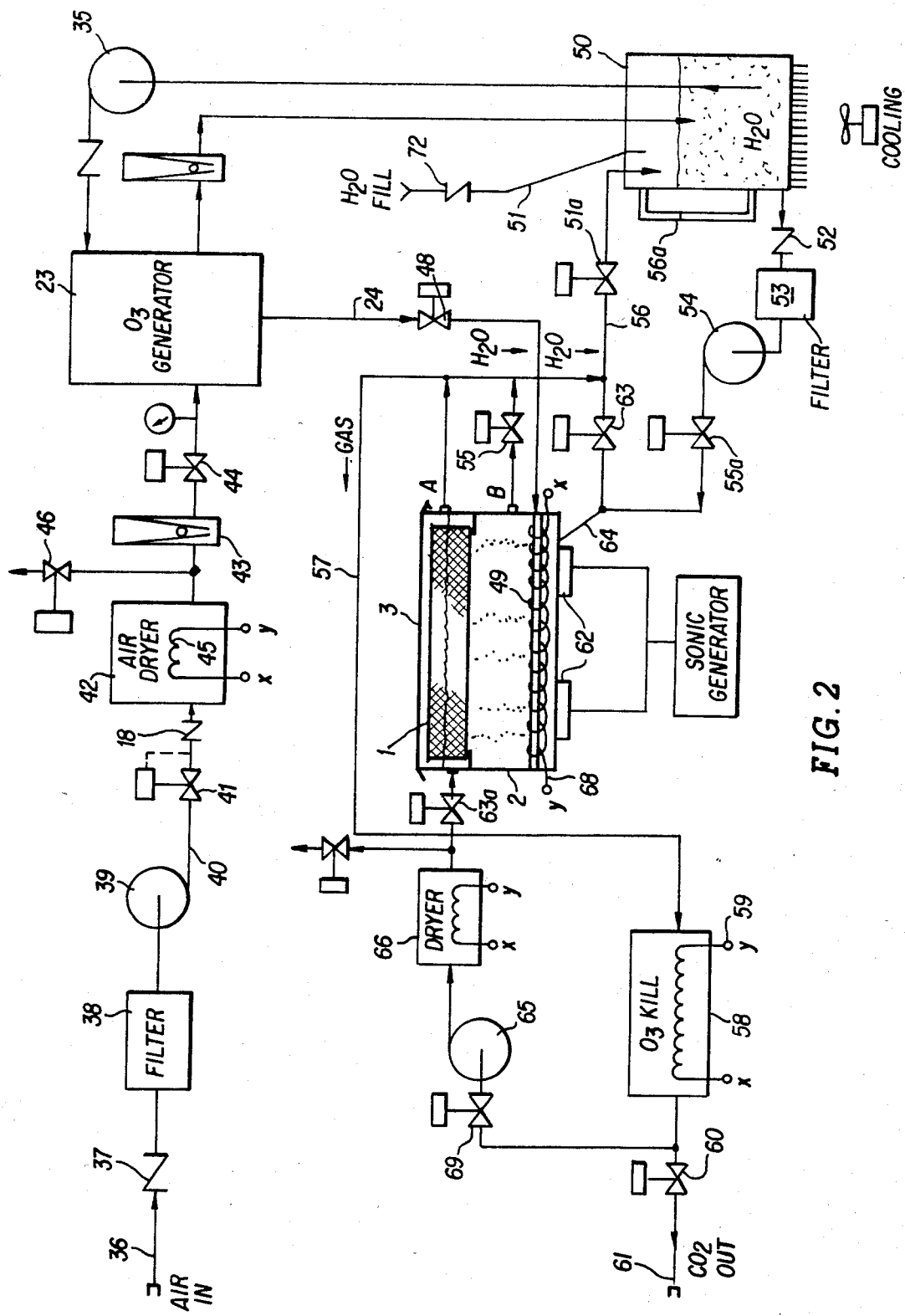

In the drawing, FIG. 1 is a diagram of a hospital sterilizer, FIG. 2 is a diagram of a field sterilizer, and FIGS. 3-9 show the sterilizing chamber at various stages in the sterilizing cycle.

In the hospital sterilizer of FIG. 1, the instruments to be sterilized are carried in a wire mesh basket 1 which allows free circulation of liquids and gases over the instruments. The basket is supported in the upper part of a tank 2 closed by a cover 3 to form the sterilizing chamber.

During the first stage of sterilization, the tank is filled with water to the level of drain line 4 connected to the building vacuum system through line 5. During this stage, if the water level rises above the line 4, the excess is drained down to that level. Water is supplied to the tank from water line 7, through strainer 8, pressure reducing valve 9, manual valve 10, flow meter 11, solenoid valve 12, and manual valve 13 discharging to the bottom of the tank. Oxygen for the generation of ozone is obtained from line 14 connected to the oxygen supply 15 and feeding the oxygen through filter 16, pressure reducing valve 17, manual valve 18, solenoid valve 19, air drier 20, and flow meter 21 to ozone generator 23. Pump 16a is only used when line pressure is not high enough. The ozone from the generator leaves through line 24 and enters the tank through a flat nozzle 25 having a large number of fine perforations 26 in its upper surface through which the ozone bubbles through the water which is maintained at the level of line 4 during the first stage of sterilization. The bubbling of the ozone through the water causes the ozone to become dissolved in the water and also creates a moist ozone vapor which flows upwardly and over the instruments in the basket 1. The moisture laden ozone is an effective sterilizing agent for all surfaces with which it comes into contact. A wetting agent added to the water further increases the effectiveness of the moist ozone. The ozone is an effective oxidizing agent which oxidizes or burns the bacteria or spores at temperatures well below steam sterilizing temperatures. This means that instruments which cannot stand steam sterilizing temperatures, pressures or vacuum can be effectively sterilized by the moist ozone. The ozone vapor is illustrated in FIG. 4 and takes about 15-25 minutes.

In the next stage, the valve in drain line 4 is closed and the valve in drain line 27 is opened and the liquid level in the tank is raised to the level of drain line 27, the instruments are immersed in ozonated water and ozone bubbles contact the instruments and have a scrubbing action tending to remove surface bacteria. This action is important for surfaces carrying more than one layer of bacteria because an outer layer of bacteria could protect an inner or underlying layer of bacteria from sterilization. The sterilization effect is greatest at the outer surface where the bacteria first comes into contact with the ozone. This stage is illustrated in FIG. 5. In the next stage, concurrently with the bubbling ozone, ultrasonic transducers 30 send ultrasonic vibrations through the water which have a scrubbing action of the surfaces of the instruments and furthermore have a pulsing effect on bacteria lodged in crevices which tend to move the ozone containing water (a sterilizing agent) into and out of the crevices and thereby dislodge bacteria which might otherwise not be reached by the sterilizing agent. During the ultrasonic cycle the ultrasonic transducers are turned off and on, being on for one second and off for a few seconds. This is to get the ultrasonic action and not to drive out of solution the $O_3$. This second stage takes about 15 minutes.

At the end of the sterilizing cycle, which is typically an interval about half the total time required for steam or gas sterilization, the water in tank 2 is drained through drain line 31 under the control of solenoid valve 32 so as to conduct the water to the hospital vacuum line 5. There is also an alternative manual drain 33. The flow of ozone continues for about 5 minutes while the tank is draining and results in some drying of the instruments. Oxygen is then flowed through the tank to finish the drying and flush out the ozone. At the end of the drying portion of the sterilizing cycle, the cover is removed and the instrument tray containing the sterilized instruments is lifted from the tank.

By way of example, the following test results are given to show the effectiveness of the sterilizer. Kill tests have been run at different concentrations of ozone on a number of different bacteria. This is a typical group.

| Bacteria | Kill Time Using 2% Ozone |
| --- | --- |
| *Escherichia coli* | 4 minutes |
| *Staphylocollus aureus* | 5 minutes |
| *Streptocollus pyogenes* | 6 minutes |
| *Candida albicans* | 4 minutes |
| *Penicilium motatum* | 3 minutes |
| *Aspergillus niger* | 6 minutes |

*Bacillus subtilus var. globigii,* a difficult to kill spore forming bacteria, was set up as a kill standard. USP has set a kill time for sterilization at 120 minutes for this bacteria. Commercial sterilizers get a kill time of 30 to 35 minutes for 100% kill. We are producing 100% kill in 15-20 minutes employing 3.5-4.5% ozone concentration.

The kill time varies directly with ozone concentration. It will take 75 minutes to kill *Bacillus globigii* with an ozone concentration of 1.5%. At 5% concentration, less than 10 minutes exposure is required.

The portable or field sterilizer shown in FIG. 2 is designed to operate on 110 volts, 60 cycles, or on a 12 volt battery and to use air instead of oxygen and to use water which is continuously recirculated between the sterilizing chamber and a holding tank. Water from the holding tank is also circulated though the ozone generator by pump 35 for cooling.

The portable sterilizer can use the wire basket 1, tank 2 and cover 3 of the hospital sterilizer shown in FIG. 1. Other parts which are the same are indicated by the same reference numerals.

Air for the ozone generator 23 enters through a supply duct 36 manually controlled by a valve 37 and flows through a filter 38 to a pump 39 having its output 40 regulated by a pressure regulator 41 and the flow rate set by valve 18. The air then flows through an air drier 42 to remove moisture, through a flow meter 43 and control valve 44 into the ozone generator 23. The air drier 42 is equipped with a heating coil 45 which, when energized, will heat the drier and drive off the water collected. This operation is performed after each sterilizer run. Valve 44 is closed when the drier 42 is heated, and valve 46 is open to let the water vapor escape.

The output of the ozone generator 23 which is a mixture of air and ozone flows through line 24 and a flow control valve 48 into submerged tubes 49 adjacent the bottom of tank 2. The tubes which are made of stainless steel have fine holes in the upper surface along the length thereof through which the ozonated air escapes. The ozonated air bubbles up through the water and forms a moist ozone containing vapor which sterilizes the instruments in the basket 1. The ozone also dissolves in the water which itself becomes a sterilizing agent.

The water for the sterilizer is obtained from a supply tank 50 which is filled at 51 through valve 72. The water preferably contains a wetting agent. Other water soluble sterilizing agents such as hydrogen peroxide, hydrogen sulphide, HCN, iodine compounds, etc., can be added either as a supplementary or as a sole sterilizing agent. From the supply tank 50, the water flows through a manually settable valve 52 which is set at a value which determines the rate of flow and through a filter 53 to a pump 54 which discharges through a pressure regulating valve 55a to the bottom of the sterilizing tank 2. The pump 54 runs continuously during sterilization. During the first stage, valve 55 is open and water is continually withdrawn through line B and valve 55 and recirculated to the tank through line 56. This maintains a water level up to line B covering the nozzles 49 so that ozonated air under pressure bubbles through the water and creates a moist ozone vapor which sterilizes the instruments in tray 1. The level of water in the tank 50 is shown by a sight gauge 56a. During this stage, excess ozone containing air leaves the tank 2 through line 57 and flows through a filter 58 containing carbon and a heater 59 which breaks down the ozone and converts it to $CO_2$ which is discharged to the atmosphere through valve 60 and outlet line 61. The first stage of sterilizing lasts approximately 15 minutes.

At the end of the first stage, the valve 55 is closed and the pump 54 continues to run. The water level rises to outlet line A which returns the excess water through line 56 to the supply tank through valve 51a. During this stage, the instruments in the tray 1 are immersed in ozone containing water (a sterilizing agent) and ozone is released into the water in the form of ozone filled bubbles. The bubbling of ozone over the instruments has a scrubbing action which tends to dislodge surface contamination. The breaking of the bubbles in contact with the instruments also causes back and forth movement of ozone containing water into and out of crevices which might contain harmful bacteria. During this second stage, which may last an additional 15–30 minutes, ultrasonic generators 62 are intermittently energized, creating ultrasonic waves which exert a further scrubbing action on the instruments and also assist in moving the ozone containing liquid back and forth into and out of crevices. The ultrasonic generators are preferably on intermittently for a short interval, such as on one second and off for four seconds, so that the ultrasonic waves will not excessively drive the dissolved ozone out of the water.

At the end of the sterilizing cycle, the valves 48, 55a and 60 are closed and valves 63 and 51a are open. Pump 54 is stopped. The water in tank 2 drains through lines 64 and 56 to storage tank 50. The sterile ozone containing air in the tank is forced through heated carbon filter 58 which converts the ozone to $CO_2$ and $O_2$ which is returned by pump 65 through drier 66 and valve 63 to tank 2 where it picks up more ozone containing air and is recycled through filter 58 to the tank. It will take about 10 minutes for the water to drain back into storage tank 50. When the water is below nozzles 49, the pump 65 starts, valve 69 opens and valve 51a closes, and the heating coil in tank 2 at 68 will be energized heating the air. This heating action will help in drying and will help to kill the ozone. After 30 minutes, the tank 2 is ozone free and the instruments in the tray 1 are dried and the cover 3 can be removed to permit removal of the instrument tray. The drying has been accomplished by recirculating sterile air as required to remove the ozone. Drying may be accelerated by energizing the heater 68 which further heats the sterile air in the tank.

FIGS. 3–9 show the sterilizing chamber at successive stages of the sterilizing cycle.

In FIG. 3, the sterilizing chamber is ready to receive a load of instruments or other material to be sterilized.

In FIG. 4, the water is below the instruments and a mixture of ozone and gas ($O_2$ for FIG. 1; air for FIG. 2) is being bubbled through the water to form a high humidity ozone vapor which is an effective sterilizing agent.

In FIG. 5, the water level has been raised to submerge the instruments in ozone containing water (a sterilizing agent) containing bubbles of ozone containing gas which have a scrubbing action effective to dislodge surface contamination and to penetrate crevices.

In FIG. 6, intermittent ultrasonic vibrations are added to increase the scrubbing action. The ultrasonic vibrations are used during relatively short intervals to prevent driving of ozone out of the water. The dissolved ozone is retained to prevent loss of the sterilizing properties of the water.

In FIG. 7, draining of the water has started. The bubbling of the ozone continues so sterilizing action of the high humidity ozone vapor continues.

FIG. 8 shows the drying cycle. For FIG. 1, the heating element 68 is on and dry ozonated oxygen is circulated though the sterilizing chamber 2 to the vacuum line 5, picking up moisture from the instruments. For the portable sterilizer of FIG. 2, the heating element 68 is on, the ozonated air in the chamber 2 is recycled through heated ozone filter 58, drier 66 and back into the chamber 2, The ozonated air is sterile. The recycling does not contaminate the instruments. At the end of the drying cycle, the instruments are sterile and dry and the atmosphere in the sterilizing chamber is ozone free.

For sterilizing loads which are not to be immersed in water, only the stages illustrated in FIGS. 3, 4, 8 and 9 are used.

As shown in FIG. 3, material to be sterilized is loaded into the chamber which is closed and evacuated to insure uniform penetration of the sterilizing agent.

As shown in FIG. 4, a moist ozone is injected into the chamber and withdrawn through an ozone filter 58. At the end of the sterilizing cycle which typically lasts from 30–45 minutes, the water is drained, the sterile atmosphere in the chamber is heated by heating element 68 and circulated through ozone filter 58 to remove ozone and is returned to the sterilizing chamber through drier 66 where it picks up moisture from the load and is recycled. After several minutes of recycling, the load is dry, ozone free, and ready for removal from the chamber, as shown in FIG. 9. The recycling also removes chemical germicide additions.

The invention is not limited to ozone and water. Other liquids, such as alcohol, naphtha, solvents, etc., may be added to or substituted for water. The liquids may have sterilizing properties. Other sterilizing agents, such as HCN, hydrogen peroxide, hydrogen sulphide, iodine compounds, may be used in addition or as a substitute for ozone. Ozone destroys HCN so HCN must be used first followed by ozone.

I claim:

1. The method of sterilizing in which an article to be sterilized is submerged in water, and ozone from a separate ozone rich source is bubbled through the water and over said article while it is submerged thereby providing ozone concentration in excess of water saturation alone and releasing ozone from the water in the form of ozone filled bubbles which break in contact with said article and have a scrubbing action tending to dislodge surface contamination.

2. The method of claim 1 in which the ozone is dispersed in an oxygen containing gas.

3. The method of claim 1 in which the ozone is dispersed in air.

4. The method of claim 1 in which a wetting agent is added to the water in order to get into the hidden areas easier.

5. The method of claim 1 in which there is a sterile atmosphere of ozone containing air above the water and at the end of the sterilizing cycle this atmosphere is circulated through heated carbon to convert the ozone to $CO_2$ and air, and through a drier to remove moisture and returned to the sterilizing chamber for drying the sterilized material.

6. The method of sterilizing in accordance with claim 1 in which material to be sterilized is subjected to ozone and water and a chemical for killing particular harmful organisms selected from the class consisting of hydrogen peroxide, HCN, hydrogen sulphide, water soluble iodine compounds.

7. The method of sterilizing in accordance with claim 1 in which there is a sterilizing chamber surrounding said articles and which contains a sterile atmosphere containing a sterilizing agent and at the end of the sterilizing cycle a portion of this atmosphere is continually recirculated through a filter to remove or neutralize the sterilizing agent and through a drier to remove moisture and then returned to the sterilizing chamber to mix with the sterile atmosphere and to dry the sterilized material.

8. The method of claim 7 in which the sterilizing agent is ozone and the filter is heated carbon which converts the ozone to $CO_2$ and $O_2$.

9. The method of sterilizing according to claim 1, in which prior to the step of submerging the article to be sterilized in said water, said article is first subjected to moist ozone.

10. The method of claim 9 in which the submerged article is concurrently subjected to short bursts of ultrasonic vibration while it is submerged.

11. The method of claim 9 in which the ozone is dispersed in an oxygen containing gas.

12. The method of claim 9 in which the ozone is dispersed in air.

13. The method of sterilizing in which an article to be sterilized is submerged in water, and ozone from a separate ozone rich source is bubbled through the water and over the article while it is submerged, thereby providing ozone concentration in excess of water saturation alone and the submerged article is concurrently subjected to short bursts of ultrasonic vibration with dwell periods between bursts longer than the burst periods.

* * * * *